United States Patent [19]

Keil et al.

[11] Patent Number: 5,416,219
[45] Date of Patent: May 16, 1995

[54] PREPARATION OF MONOCLINIC METAZACHLOR

[75] Inventors: Michael Keil, Freinsheim; Bjoern Girgensohn, Manheim; Gotthard Synnatschke, Ludwigshafen; August Wigger, Neuhofen; Hans Ziegler, Mutterstadt; Walter Gueckel, Limburgerhof, all of Germany

[73] Assignee: BASF Aktiengesellschaft, Ludwigshafen, Germany

[21] Appl. No.: 179,699

[22] Filed: Jan. 11, 1994

Related U.S. Application Data

[60] Division of Ser. No. 47,290, Apr. 19, 1993, Pat. No. 5,300,652, which is a division of Ser. No. 920,815, Jul. 24, 1992, Pat. No. 5,250,503, which is a continuation of Ser. No. 551,778, Jul. 12, 1990, abandoned.

[30] Foreign Application Priority Data

Jul. 29, 1989 [DE] Germany ............... 39 25 253.1

[51] Int. Cl.⁶ ......................................... C07D 231/12
[52] U.S. Cl. ............................................. 548/375.1
[58] Field of Search .................................. 548/375.1

[56] References Cited

U.S. PATENT DOCUMENTS 4,593,104  1/1986  Eicken .................. 548/375.1

Primary Examiner—Robert W. Ramsuer
Attorney, Agent, or Firm—Keil & Weinkauf

[57] ABSTRACT

Monoclinic 2-chloro-(2',6'-dimethyl-N-pyrazol-1-ylmethyl)-acetanilide of the formula

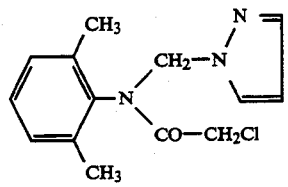

which melts at 76° C. Processes for its preparation and herbicides.

1 Claim, No Drawings

PREPARATION OF MONOCLINIC METAZACHLOR

This is a Division of application Ser. No. 08/047,290, filed Apr. 19, 1993 now U.S. Pat. No. 5,300,652 which is a Division of application Ser. No. 07/920,815 filed Jul. 24, 1992 now U.S. Pat. No. 5,250,503 which is a FWC of application Ser. No. 97/551,778 filed Jul. 12, 1990, now abandoned.

The present invention relates to monoclinic 2-chloro-(2',6'-dimethyl-N-pyrazol-1-ylmethyl)-acetanilide of the formula I

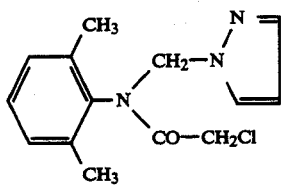

which melts at 76° C., and processes for the preparation of this modification, its use as a herbicide, and herbicides which contain this active ingredient.

The important herbicidal active ingredient 2-chloro-(2',6'-dimethyl-N-pyrazol-1-ylmethyl)-acetanilide I (common name: metazachlor) melts, as far as is known, in a range of 78°–83° C. and crystallizes in a triclinic crystalline form. This crystalline form IA is obtained by the methods described in DE-A 2 648 008, DE-A 2 830 764 and EP-A 12216, by crystallization of I from a nonpolar or slightly polar solvent, such as cyclohexane or toluene.

However, this known modification IA of metazachlor, which is commercially available in the form of concentrated aqueous suspensions, has the disadvantage that it frequently forms agglomerates.

The agents then cannot be sprayed uniformly, if at all.

In efforts aimed at remedying this deficiency, a monoclinic modification of I, which modification melts at 76° C., was found.

This monoclinic modification IB is obtained if water is added to an aqueous metazachlor solution containing sulfuric acid, at from 0° to 50° C., in the presence of a water-miscible polar inert organic solvent, and the resulting solid is isolated in a conventional manner after crystallization is complete.

In this process, the order in which the active ingredient solution, the organic solvent and the water are mixed with one another is unimportant for the crystallization.

Seeding with crystals of modification IB is not essential but generally proves advantageous.

Particular suitable protic polar inert solvents are alcohols, such as methanol, ethanol, isopropanol, n-propanol, 1-butanol, 2-butanol, isobutanol, tert-butanol, ethylene glycol, propylene glycol, propane-1,3-diol and butanediols, ketones, such as acetone and butan-2-one, ethers, such as tetrahydrofuran and 1,4-dioxane, amides, such as dimethylformamide and N-methylpyrrolidone, and dimethyl sulfoxide and diethylene glycol.

The seed crystals required for the preparation of metazachlor in modification IB in amounts of from 0.01 to 50% by weight can be obtained for the first time, for example, by recrystallization of metazachlor of modification IA from the abovementioned polar organic solvents.

In another possible method for the preparation of metazachlor of modification IB, from 0.01 to 50% by weight of seed crystals of modification IB are added to an aqueous suspension of metazachlor of modification IA at a pH of from 0 to 10, with or without the addition of one or more of the abovementioned water-soluble organic solvents, at from 0° to 45° C., and stirring is carried out at from 0.1 to 20 hours. Modification IA is transformed into modification IB.

This transformation also takes place in a similar manner when an aqueous suspension of the triclinic modification IA melting at 79° C. is milled at from 0° to 45° C. in the presence of a polar water-miscible inert organic solvent in the presence of crystals of the compound in the monoclinic crystalline modification melting at 76° C.

TABLE

| Method of measurement | Unit | IA | IB |
|---|---|---|---|
| Differential thermal analysis | °C. | 79 | 76 |
| IR spectroscopy* | cm$^{-1}$ | 3160, 1300 | 1360, 780 |
| X-ray diffraction pattern (diffraction angle 2 $\theta$) | degrees | 8.2; 8.4 | 9.9; 12.3 |
| Solid-state $^{13}$C-NMR spectroscopy* (against adamantane) | $\delta$ in ppm | 62.5; 137.1 | 51.4; 139.1 |
| Modification from X-ray structural analysis | — | triclinic | monoclinic |
| Microscopy (crystal form) | — | amorphous | coffin-lid-shaped |

*Selected signals

The effect of the invention is as follows: Formulated product containing metazachlor of the known modification IA changes during storage. The size of the suspended particles increases continuously; in the formulated product, this is evident in the formation of fragments right up to complete solidification of the previously liquid product, so that uniform application of the product is no longer ensured.

Formulated product containing metazachlor of modification IB does not have this undesirable behavior and can be applied satisfactorily even after prolonged storage.

During these investigations, a further metastable metazachlor modification IC which melts at 84° C. was found. This modification is obtained by heating metazachlor of modification IA to 84° C. and milling the melt formed.

On standing, the metazachlor modification IC, which has a half-life of about 5 days, is transformed into modification IB, which melts at 76° C.

The Examples which follow illustrate the novel process:

1. Precipitation of an acidic aqueous metazachlor solution with seeding with modification IB.
   a) 1,250 ml of water and 22 ml of methanol are initially taken at 25° C. For seeding, 3.8 g of metazachlor of modification IB are added. 62.5 g of a 40% strength metazachlor solution in 60% strength sulfuric acid are then added slowly while stirring, stirring is continued for one hour and a further 562.5 g of the metazachlor solution are then added rapidly. After complete precipitation, the precipitate is isolated, washed with water and dried. 247 g of metazachlor of modification IB are obtained.

b) 7.6 g of methanol and 51 g of water are added to a solution of 63 g of metazachlor of modification IA in 90 g of 60% strength sulfuric acid, while stirring, at 40° C. After the addition of 3 g of metazachlor of modification IB, 133 ml of water are added in the course of two hours and then a further 113 ml of water are added rapidly. Stirring is continued for two hours and the product is filtered off under suction, washed with 200 ml of water and then dried. 62.3 g of metazachlor of modification IB are obtained.

2. Preparation of metazachlor of modification IB by transformation of the crystalline modification IA in aqueous suspension.

1 g of modification IB is added to a suspension of 10 g of metazachlor of modification IA in 127 g of 15% strength sulfuric acid and 2 g of methanol, the mixture is stirred for 20 hours at 20° C. and the product is filtered off under suction and washed with 500 ml of water. Metazachlor of modification IB is obtained.

3. Preparation of metazachlor of modification IB by crystallization from methanolic aqueous solution.

A mixture of 2.2 l of methanol and 1,500 g of metazachlor of modification IA is converted into a solution at 50° C. The solution is slowly allowed to reach room temperature, and 5.2 l of water are slowly added to the partially crystallizing mixture. Filtration under suction and washing with 1 l of water give 1,485 g of metazachlor of modification IB.

We claim:

1. A process for the preparation of crystalline monoclinic-2-chloro-(2',6'-dimethyl-N-pyrazazol-1-ylmethyl)-acetanilide of the formula I

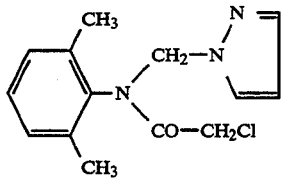

which melts at 76° C. which process comprises milling an aqueous suspension of the compound I in the triclinic crystalline modification of I, which modification melts at 79° C. at from 0° to 45° C., with a polar water-miscible inert organic solvent in the presence of crystals of the compound I in the monoclinic crystalline modification melting at 76° C.

* * * * *